United States Patent [19]
Badertscher

[11] Patent Number: 6,017,569
[45] Date of Patent: Jan. 25, 2000

[54] HYDROLYZING CEREAL WITH FRUIT OR HONEY PRESENT AND APPARATUS THEREFOR

[75] Inventor: Ernest Badertscher, Orbe, Switzerland

[73] Assignee: Nestec S.A., Vevey, Switzerland

[21] Appl. No.: 08/752,351

[22] Filed: Nov. 19, 1996

[30] Foreign Application Priority Data

Nov. 20, 1995 [EP] European Pat. Off. .............. 95203172

[51] Int. Cl.$^7$ ..................................... A23L 1/164
[52] U.S. Cl. ................ 426/28; 426/18; 426/49; 426/52; 426/618; 426/619; 426/620; 426/621
[58] Field of Search ................................ 426/18, 44, 28, 426/49, 52, 618–621

[56] References Cited

U.S. PATENT DOCUMENTS

| | | | |
|---|---|---|---|
| 3,219,483 | 11/1965 | Goos et al. ................................. | 127/28 |
| 3,870,803 | 3/1975 | Siems et al. . | |
| 4,089,984 | 5/1978 | Gilbertson ................................ | 426/293 |
| 4,374,860 | 2/1983 | Gasser et al. . | |
| 4,834,988 | 5/1989 | Karwowski et al. ..................... | 426/20 |
| 4,857,356 | 8/1989 | Reinl et al. . | |
| 4,900,565 | 2/1990 | Spies ........................................ | 426/88 |
| 5,395,569 | 3/1995 | Radertscher et al. . | |

FOREIGN PATENT DOCUMENTS

0619083A1  3/1994  European Pat. Off. .

OTHER PUBLICATIONS

Whistler, et al., Ed., Starch: Chemistry and Technology, vol. II, Industrial Aspects, Academic Press, N.Y., 1967, pp. 147, 153–157.

*Primary Examiner*—Donna Wortman
*Assistant Examiner*—Brenda G. Brumback
*Attorney, Agent, or Firm*—Vogt & O'Donnell, LLP

[57] ABSTRACT

A hydrolyzed cereal product containing honey or whole fruit or pieces of fruit is obtained by preparing a mixture of cereal flour and *alpha*-amylase and also honey or fruit, the fruit being whole or in pieces, passing a stream of the mixture through an assembly so that the mixture is treated successively by jets of steam which are injected to envelope the mixture stream to heat the stream first to hydrolyze starch of the cereal flour and so that after the first steam-treatment, wherein the steam jet may be directed to the mixture stream co- or counter-currently, the subsequent successive steam jet or jets are directed to the hydrolyzed product stream counter-currently. Apparatus for carrying out the process includes two nozzles which have conically-shaped ends positioned to form a channel which communicates which a steam-supply passage of a T-shaped body.

12 Claims, 2 Drawing Sheets

HYDROLYZING CEREAL WITH FRUIT OR HONEY PRESENT AND APPARATUS THEREFOR

BACKGROUND OF THE INVENTION

The present invention relates to hydrolyzed cereals containing fruit or honey and to processes and apparatus for preparation of the same.

The manufacture of hydrolyzed cereals has been known for a long time.

European Patent Application Publication No. 0 258 486 EP 258486 describes, in particular, a process for preparing hydrolyzed cereals with added fruits, in which 20 to 25% of enzymatically hydrolyzed cereals are first prepared and then mixed with oatmeal, with water and with at least 50% fruit. The mixture is then heated, it is degassed and it is subjected to a post-heating stage, before packaging it in glass containers which are pasteurized.

The dry matter content of the fruits is very low. It is in general of the order of 10 to 15%. This poses problems in the preparation of hydrolyzed cereals with added fruits since it increases the duration and the cost of drying and, furthermore, this impairs the quality of the product.

Honey often contains many spores. This poses problems during the preparation of hydrolyzed cereals with added honey, because if the honey is added just before the sterilization stage, the increase in the bacterial load through germination of the spores during the sterilization stage is not prevented.

SUMMARY OF THE INVENTION

The subject of the present invention is to provide a process for preparing hydrolyzed cereals with added fruits or honey as well as an apparatus for carrying out the process under particularly simple conditions which make it possible to avoid the problems stated above.

To this end, in the process for preparing hydrolyzed cereals with added fruits or honey according to the present invention:

a mixture is prepared comprising a cereal flour, whole fruits and/or fruit pieces and an *alpha*-amylase, or a mixture comprising a cereal flour, honey, water and an *alpha*-amylase to hydrolyze starch of the cereal flour to provide a hydrolysis product.

the mixture is treated by injecting steam in successive stages in successive treatment zones in series, the steam being injected in the form of an annular jet enveloping the mixture, counter-current to or co-current with the direction of the stream of mixture in a first zone and counter-currentwise in the following zones, with the quantity of steam decreasing from stage to stage and, then the mixture is dried.

The apparatus according to the present invention comprises, mounted in series, at least 2 steam injecting devices, each comprising a product injection nozzle part and a product ejection nozzle part and each having an inner section initially convergent and then divergent, which are placed one after the other in a straight tube of a T-shaped body, characterized in that a downstream end of the injection nozzle has a conical inner surface opening out towards the downstream end, an upstream end of the ejection nozzle has a conical outer surface converging towards the upstream end, the said upstream end of the ejection nozzle penetrates into the downstream end of the injection nozzle, and both ends delimit between them a conical steam injection passage converging and opening out through an annular outlet orifice in the product injection nozzle and having an annular inlet orifice adjacent to a tubular arm of the T-shaped body.

It has been observed, surprisingly, that such a process and such an apparatus effectively make it possible to increase the dry matter content of the mixture by directly hydrolyzing the cereal flour mixed with the fruits while avoiding damaging the whole fruits or fruit pieces by treating the mixture by injecting steam in successive stages and counter-currentwise.

Furthermore, it has been observed, surprisingly, that such a process and such an apparatus effectively make it possible to obtain hydrolyzed cereals with added honey which are free of bacterial load by directly hydrolyzing the cereal flour mixed with the honey and by sterilizing the mixture by injecting steam, in successive stages, counter-currentwise. Indeed, during hydrolysis of the mixture, the spores contained in the honey germinate and, during sterilization, all this bacterial load is removed.

DETAILED DESCRIPTION OF THE INVENTION

To carry out the process according to the present invention, a mixture is preferably prepared having a water content of 40–80%.

In a first preferred embodiment of the present process, a mixture may be prepared comprising, in % by weight of dry matter, 15–45% of fruits and 85–55% of cereal flour for example.

In a second preferred embodiment of the present process, a mixture may be prepared comprising 15–25% of honey, 40–50 % of water and 30–40% of cereal flour for example.

Preferably, a mixture is prepared comprising 0.05 to 0.2 g of *alpha*-amylase per 100 g of cereal flour dry matter. There may be used especially as *alpha*-amylase that marketed under the name DEXLO P by Gist-Brocades N.V., Food Ingredient Division, P.B. 01, NL-260 MA DELFT.

The said mixture is therefore treated by passing the mixture in a direction through successive treatment zones and injecting steam in successive stages in the successive treatment zones, the steam being injected in the form of an annular jet enveloping the mixture, counter-current to or co-current with the direction of the stream of the mixture in a first zone and counter-currentwise in the following zones.

The fact that the steam may be injected into a first treatment zone in the direction of the stream of the mixture, i.e., co-currently whereas in the following zones it can be injected counter-currently to the mixture, is to avoid damaging, where appropriate, the relatively fragile fruit pieces and/or whole fruits for example.

Preferably, the mixture is treated with a quantity of steam which decreases from stage to stage, starting with a temperature of 80–100° C., which is favourable to the hydrolysis, up to a temperature of 120–150° C., which is necessary for the sterilization and for the inactivation of the enzymes.

At each stage, the steam injecting device is connected to the principal steam inlet conduit by a tubular arm. The opening of the steam injection nozzles decreases from stage to stage, so as to gradually reduce the quantity of steam injected between the first and the last stage.

In the first preferred embodiment of the present process, the mixture preferably crosses the successive treatment zones in the form of a cylindrical stream with a diameter greater than the size of the whole fruits and/or fruit pieces, so as not to damage the whole fruits and/or fruit pieces.

Finally, the mixture can be dried especially by freeze-drying, in the case of a mixture comprising a cereal flour and whole fruits and/or fruit pieces or by spraying, in the case of a mixture comprising a cereal flour, honey and water for example.

In the first preferred embodiment of the present process, the fruits may be chosen from a group comprising raspberries, strawberries and cherries for example.

Preferably, in a preferred embodiment of the present process, the pH of the fruits is adjusted to a value of between more than 5 and 6.5 by preparing the mixture in the presence of an alkali metal salt, so as to be able directly to hydrolyze the cereal flour with the fruits with *alpha*-amylase at optimum pH. Trisodium phosphate may be used as alkali metal salt for example.

Preferably, the mixture comprising a cereal flour and whole fruits and/or fruit pieces is then acidified to pH 3–5 before drying with an alkali salt, so as to restore the colour of the fruits which they might have lost because of the increase in their pH to a value of between more than 5 and 6.5. The mixture may be acidified with citric acid monohydrate for example.

The apparatus used according to the present invention is described in greater detail below with reference to the accompanying drawings:

DETAILED DESCRIPTION OF THE DRAWINGS

Figure 1:
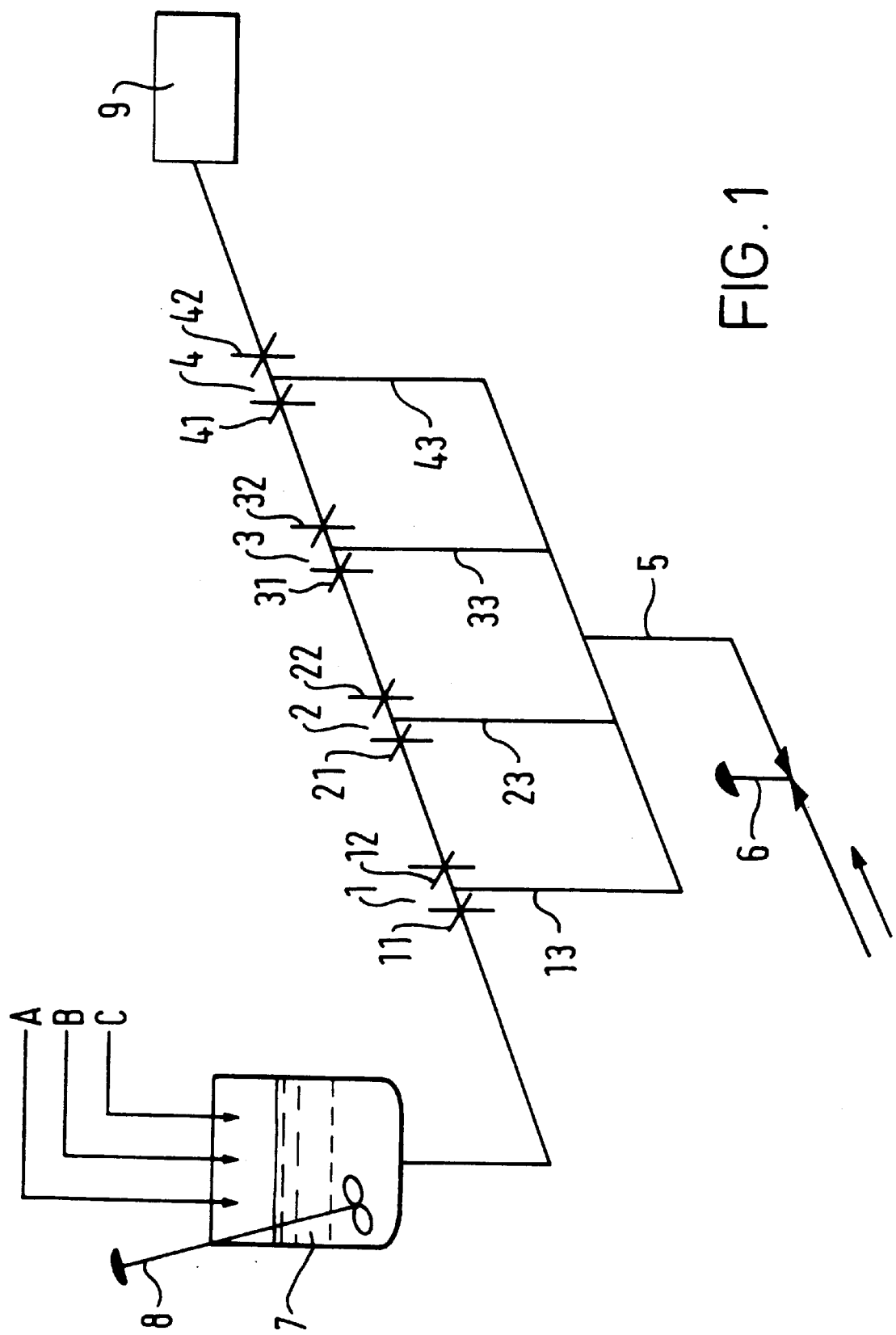
FIG. 1 is a general schematic view of an embodiment of the apparatus.

The embodiment of the apparatus represented in FIG. 1 comprises four steam injecting devices (1,2,3,4) mounted in series.

Each steam injecting device comprises a product injection nozzle (11,21,31,41) and a product ejection nozzle (12,22,32,42).

Each steam injecting device has a tubular arm (13,23,33,43) connected to the principal steam inlet conduit (5) provided with a control valve (6). The first steam injecting device is connected to the reservoir (7) provided with a mixer (8), in which the mixture is prepared comprising a cereal flour (A), whole fruits or fruit pieces or honey and water (B) and an *alpha*-amylase (C).

The last steam injecting device is connected to the drying device (9).

Figure 2:
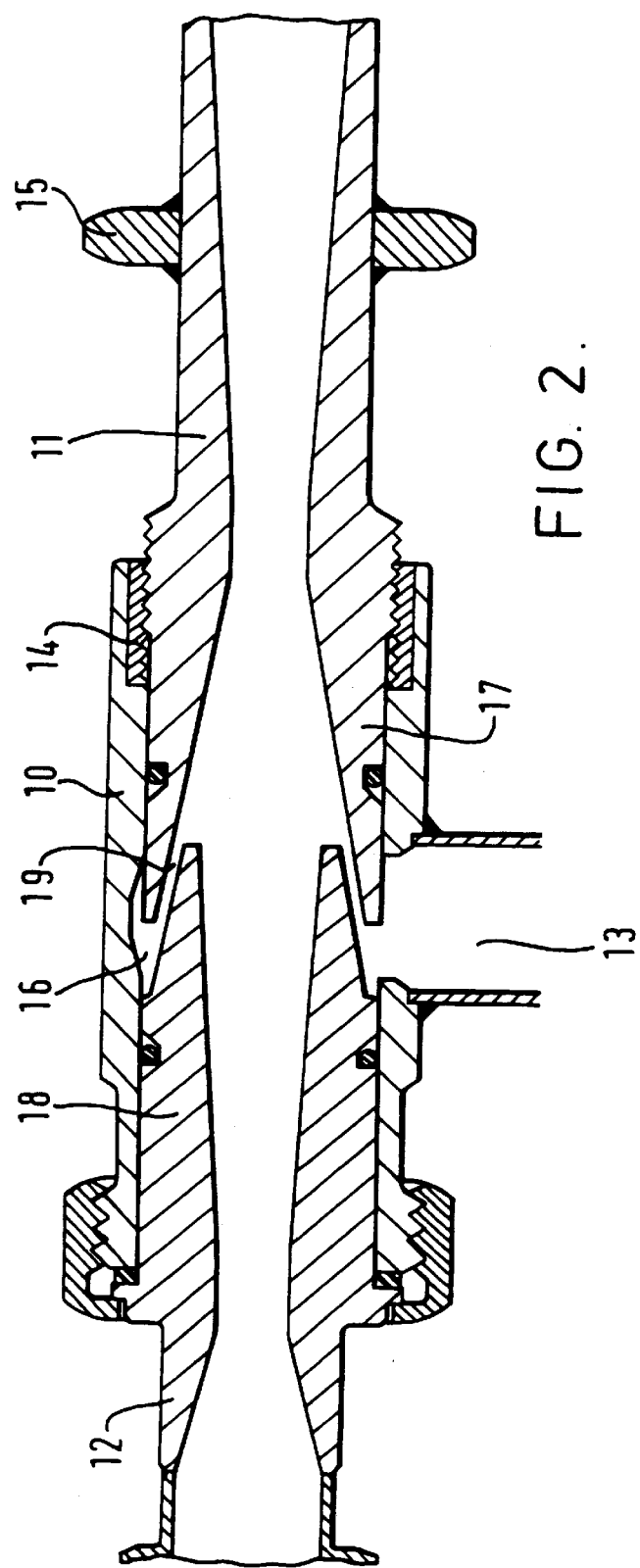
FIG. 2 is a longitudinal cross section of a steam injecting device of the apparatus represented in FIG. 1.

As can be seen in FIG. 2, the steam injecting device comprises a product injection nozzle (11) and a product ejection nozzle (12) one after the other in the straight tube (10) of the T-shaped body, as well as a tubular arm (13) which provides a passage allowing the inlet of steam through the annular orifice (16). The straight tube (10) is provided with an adjusting nut (14) and with a forcing nut (15).

The upstream end (18) of the product ejection nozzle (12) penetrates into the downstream end (17) of the product injection nozzle (11). As indicated in the Summary above and as shown in drawing FIG. 2, the downstream end (17) of the injection nozzle (11) has a conical inner surface opening out towards the downstream end. The upstream end (18) of the ejection nozzle (12) has a conical outer surface converging towards the upstream end. The conical surfaces of the two ends delimit between them a conical steam injection passage (19) opening out to and communicating with a steam outlet orifice from the passage (19). Additionally, as also illustrated in drawing FIG. 2, each of the nozzles (11) and (12) has an interior surface which extends longitudinally and has a shape which defines first and second portions wherein the first portion (upstream), along its longitudinal extent, converges and extends downstream to the second portion and wherein the second portion, along its longitudinal extent away from the first portion diverges.

EXAMPLES

The product according to the present invention is described in greater detail in the examples below where the percentages and parts are given by weight.

Example 1

Using an apparatus such as that represented in the drawings, hydrolysed cereals with added raspberries are produced.

A mixture is prepared in the reservoir comprising 72 kg of wheat flour (87% dry matter), 199 kg of fresh raspberries (13% dry matter), 0.1 kg of *alpha*-amylase DEXLO P and 5 kg of trisodium phosphate.

The mixture has a water content of 66% and a pH of 5.7.

The mixture thus prepared is treated by injecting steam in four stages with the quantity of steam decreasing from stage to stage. In the first steam injecting device, the temperature is 90° C., so as to allow the hydrolysis and, then in the other three steam injecting devices, the temperature increases gradually up to 130° C., so as to allow sterilization of the mixture without damaging the raspberry pieces.

After sterilization, the mixture is cooled to 65° C. and the mixture is acidified to pH 4 by adding 5 kg of prediluted citric acid monohydrate to it.

Finally, the mixture is dried by freeze-drying.

A mixture of hydrolyzed cereals with added raspberries is thus obtained whose composition is the following:

protein 10.3%
fat 1.4%
carbohydrate 66.7%
fibre 12.3%
ash 6.3%
water content 3%

Example 2

Using an apparatus such as that represented in the drawings, hydrolysed cereals with added black cherries are produced.

A mixture is prepared in the reservoir comprising 63 kg of wheat flour (87% dry matter), 202 kg of stoned black cherries (19.8% dry matter), 0.1 kg of *alpha*-amylase DEXLO P and 1.4 kg of trisodium phosphate.

The mixture has a water content of 63.7% and a pH of 5.5.

The mixture thus prepared is treated by injecting steam in four stages with the quantity of steam decreasing from stage to stage. In the first steam injecting device, the temperature is 90° C., so as to allow the hydrolysis and, then in the other three steam injecting devices, the temperature increases gradually up to 130° C., so as to allow sterilization of the mixture without damaging the cherry pieces.

After sterilization, the mixture is cooled to 65° C. and the mixture is acidified to pH 4.2 by adding 1.7 kg of prediluted citric acid monohydrate to it.

Finally, the mixture is dried by freeze-drying.

Hydrolysed cereals with black cherries are obtained whose composition is the following:

protein 7.9% fat 0.9% carbohydrate 79.8% fibre 5.6% ash 2.7% water content 3%

Example 3

Using the apparatus as represented in the drawings, hydrolysed cereals with added honey are prepared.

To this end, a mixture comprising 72.8 kg of flour, 43.1 kg of Mexican honey, 100.4 kg of water and 0.1 kg of *alpha*-amylase is prepared in the reservoir.

The mixture has a water content of 53.7%.

The mixture thus prepared is treated by injecting steam in two stages with the quantity of steam decreasing between the first and the second stage. In the first steam injecting device, the temperature is 93° C., so as to allow the enzymatic reaction and then in the second steam injecting device, the temperature increases gradually up to 140° C., so as to allow sterilization of mixture and inactivation of the enzymes.

After sterilization, the mixture is cooled to 65° C. and then it is spray-dried.

A mixture of hydrolyzed cereals with added honey is thus obtained whose composition is the following:

protein 7.9% fat 0.8% carbohydrate 85.8% fibre 3% ash 0.5% water content 2%

I claim:

1. A process for preparing a hydrolyzed cereal product comprising:

preparing a mixture which comprises a cereal flour, *alpha*-amylase and fruit selected from the group consisting of whole fruit and pieces from whole fruit and which comprises a water content of from 40% to 80% by weight;

passing a stream of the mixture in a direction through an annular tubular assembly and injecting a first annular jet of steam and at least one further annular jet of steam in series with the first steam jet within the assembly so that the steam jets envelope the mixture stream passing through the assembly to treat the mixture so that the mixture stream is treated successively by the steam jets first to heat the mixture so that starch of the cereal flour is hydrolyzed by the *alpha*-amylase to obtain a hydrolysis product stream and so that subsequently, the hydrolysis product stream is steam-treated and injecting the first steam jet so that the jet is directed to the mixture stream in a direction which is one of either a direction which is co-current with or a direction which is counter-current to the mixture stream flow direction, and injecting each further steam jet so that each further jet is directed to the hydrolysis product stream in a direction counter-current to the hydrolysis product stream flow direction and so that quantities of steam injected in series successive to the first steam jet decrease in each successive further steam jet injection;

obtaining a steam-treated product from the assembly; and drying the steam-treated product obtained from the assembly to obtain a dried product.

2. The process according to claim 1 wherein the hydrolysis product stream is steam-treated to sterilize the mixture.

3. The process according to claim 1 wherein the first steam jet is injected so that the jet is directed co-currently with the mixture stream flow direction.

4. The process according to claim 1 or 3 wherein the mixture and hydrolysis product streams have a diameter greater than a size of the fruit.

5. The process according to claim 1 further comprising preparing the mixture with an alkali metal salt so that the mixture has a pH of from 5 to 6.5.

6. The process according to claim 5 further comprising, prior to drying, acidifying the steam-treated product to obtain an acidified product having a pH of from 3 to 5, and then drying the acidified product.

7. The process according to claim 1 wherein the steam-treated product obtained is freeze-dried.

8. The process according to claim 1 wherein the fruit is selected from the group consisting of raspberries, strawberries, blackberries and cherries.

9. A process for preparing, a hydrolyzed cereal product comprising:

preparing a mixture which comprises a cereal flour, *alpha*-amylase and honey and which comprises a water content of from 40% to 80% by weight;

passing a stream of the mixture in a direction through an annular tubular assembly and injecting a first annular jet of steam and at least one further annular jet of steam separate from the first steam jet within the assembly so that the steam jets envelope the mixture stream passing through the assembly to treat the mixture so that the mixture stream is treated successively by the steam jets first to heat the mixture so that starch of the cereal flour is hydrolyzed by the *alpha*-amylase and so that spores contained in the honey germinate to obtain a hydrolysis product stream and so that subsequently, the hydrolysis product stream is steam-treated to sterilize the hydrolysis product stream and injecting the first steam jet so that the jet is directed to the mixture stream in a direction which is one of either a direction which is co-current with or a direction which is counter-current to the mixture stream flow direction, and injecting each further steam jet so that each further jet is directed to the hydrolysis product stream in a direction counter-current to the hydrolysis product stream flow direction and so that quantities of steam injected in series successive to the first steam jet decrease in each successive further steam jet injection;

obtaining a steam-treated product from the assembly; and drying the steam-treated product obtained from the assembly to obtain a dried product.

10. The process according to claim 1 or 2 or 9 wherein the mixture stream is steam-treated to heat the mixture to a temperature of from 80° C. to 100° C. and the hydrolysis product stream is steam-treated to heat the product to a temperature of from 120° C. to 150° C.

11. The process according to claim 1 or 2 or 9 wherein the hydrolysis product stream is steam-treated with at least three separate injections of steam in series.

12. The process according to claim 1 or 2 wherein the mixture comprises the *alpha*-amylase in an amount of from 0.05 g to 0.2 g per 100 g cereal flour dry matter.

* * * * *

UNITED STATES PATENT AND TRADEMARK OFFICE
CERTIFICATE OF CORRECTION

PATENT NO. : 6, 017, 569
DATED : January 25, 2000
INVENTOR(S) : Ernest BADERTSCHER It is certified that error appears in the above-identified patent and that said Letters Patent is hereby corrected as shown below:

Column 3, line 18, after "alkali", insert -- metal --.

Column 6, line 63 (line 1 of claim 12), delete "2" and insert therefor -- 9 --.

Signed and Sealed this

Seventh Day of November, 2000

Attest:

Q. TODD DICKINSON

*Attesting Officer*  *Director of Patents and Trademarks*